United States Patent
Bainbridge et al.

(10) Patent No.: US 10,738,669 B2
(45) Date of Patent: Aug. 11, 2020

(54) SYSTEMS FOR IN SITU MONITORING OF WORKING FLUIDS AND WORKING FLUID SYSTEMS

(71) Applicant: ExxonMobil Research and Engineering Company, Annandale, NJ (US)

(72) Inventors: Samuel C. Bainbridge, Houston, TX (US); John A. Salvatore, Elmer, NJ (US); Riccardo Conti, Medford, NJ (US); William J. Hackney, Sicklerville, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 210 days.

(21) Appl. No.: 15/805,302

(22) Filed: Nov. 7, 2017

(65) Prior Publication Data
US 2018/0156086 A1    Jun. 7, 2018

Related U.S. Application Data

(60) Provisional application No. 62/431,101, filed on Dec. 7, 2016.

(51) Int. Cl.
*F01M 11/10* (2006.01)
*G01M 15/05* (2006.01)
(Continued)

(52) U.S. Cl.
CPC ............. *F01M 11/10* (2013.01); *B01D 29/60* (2013.01); *B01D 35/005* (2013.01);
(Continued)

(58) Field of Classification Search
CPC .. F01M 11/10; F01M 1/10; F01M 2001/1007; F01M 2011/1406;
(Continued)

(56) References Cited

U.S. PATENT DOCUMENTS

| | | | |
|---|---|---|---|
| 4,733,556 A * | 3/1988 | Meitzler ................ | B01D 27/08 340/631 |
| 4,852,693 A | 8/1989 | Nakajima et al. | |

(Continued)

FOREIGN PATENT DOCUMENTS

| CN | 203929565 U | 11/2014 |
|---|---|---|
| DE | 10000148 A1 | 7/2001 |

(Continued)

OTHER PUBLICATIONS

PCT/US2017/060334 International Search Report and Written Opinion dated Mar. 26, 2018.

*Primary Examiner* — Daniel S Larkin
*Assistant Examiner* — Anthony W Megna Fuentes
(74) *Attorney, Agent, or Firm* — Anthony G. Boone

(57) ABSTRACT

A working fluid monitoring system for monitoring a working fluid of working fluid system of a piece of equipment is provided. The working fluid monitoring system can include a filter member having an inlet, an outlet, and a filter media disposed between the inlet and the outlet. The filter member can be configured to permit fluid communication of the working fluid of the working fluid system from the inlet, through the filter media, and out the outlet of the filter member. A sensor is in operable communication with the working fluid within the filter member and is configured to monitor in situ a parameter of the working fluid and/or the working fluid system.

3 Claims, 3 Drawing Sheets

(51) Int. Cl.
| | |
|---|---|
| *F01M 11/12* | (2006.01) |
| *G01N 29/02* | (2006.01) |
| *G01N 33/30* | (2006.01) |
| *G01N 9/36* | (2006.01) |
| *G01M 15/04* | (2006.01) |
| *G01N 33/26* | (2006.01) |
| *G01N 11/00* | (2006.01) |
| *F16N 29/04* | (2006.01) |
| *F01M 1/10* | (2006.01) |
| *G01M 15/09* | (2006.01) |
| *B01D 35/00* | (2006.01) |
| *B01D 35/30* | (2006.01) |
| *B01D 29/60* | (2006.01) |
| *F01M 1/16* | (2006.01) |
| *G01N 33/28* | (2006.01) |

(52) U.S. Cl.
CPC .............. *B01D 35/306* (2013.01); *F01M 1/10* (2013.01); *F01M 11/12* (2013.01); *F16N 29/04* (2013.01); *G01M 15/042* (2013.01); *G01M 15/05* (2013.01); *G01M 15/09* (2013.01); *G01N 9/36* (2013.01); *G01N 11/00* (2013.01); *G01N 29/02* (2013.01); *G01N 33/26* (2013.01); *G01N 33/28* (2013.01); *G01N 33/2817* (2013.01); *G01N 33/2835* (2013.01); *G01N 33/2847* (2013.01); *G01N 33/2858* (2013.01); *G01N 33/2888* (2013.01); *G01N 33/30* (2013.01); *F01M 2001/1007* (2013.01); *F01M 2001/165* (2013.01); *F01M 2011/1406* (2013.01); *F01M 2011/148* (2013.01); *F01M 2011/1413* (2013.01); *F01M 2011/1446* (2013.01); *F01M 2011/1473* (2013.01); *F01M 2011/1493* (2013.01); *F16N 2200/02* (2013.01); *F16N 2200/08* (2013.01); *F16N 2200/20* (2013.01); *F16N 2250/00* (2013.01); *F16N 2250/08* (2013.01); *F16N 2250/18* (2013.01); *F16N 2250/32* (2013.01); *F16N 2250/34* (2013.01); *F16N 2270/50* (2013.01); *F16N 2270/56* (2013.01); *G01N 2291/0226* (2013.01)

(58) Field of Classification Search
CPC ...... F01M 2011/148; F01M 2011/1473; F01M 2011/1446; F01M 2011/1413; F01M 2011/1493; F01M 11/12; F01M 2001/165; F16N 29/04; F16N 2250/00; F16N 2250/08; F16N 2250/32; F16N 2250/34; F16N 2270/50; F16N 2250/18; F16N 2200/02; F16N 2200/08; F16N 2200/20; F16N 2270/56; G01N 33/2888; G01N 33/30; G01N 11/00; G01N 33/26; G01N 33/28; G01N 33/2835; G01N 33/2847; G01N 33/2858; G01N 9/36; G01N 2291/0226; G01N 29/02; G01N 33/2817; B01D 29/60; B01D 35/306; B01D 35/005; G01M 15/09; G01M 15/042; G01M 15/05

See application file for complete search history.

(56) References Cited

U.S. PATENT DOCUMENTS

| | | | |
|---|---|---|---|
| 6,853,203 | B2 | 2/2005 | Beylich et al. |
| 7,086,280 | B2 * | 8/2006 | Wakeman .......... G01N 33/2888 73/53.05 |
| 7,523,646 | B2 | 4/2009 | Klun |
| 8,945,400 | B2 * | 2/2015 | Reinosa ............... B01D 27/103 123/196 A |
| 2003/0046985 | A1 | 3/2003 | Schoess |
| 2006/0230833 | A1 | 10/2006 | Liu et al. |
| 2006/0254986 | A1 | 11/2006 | Hanson et al. |
| 2007/0074562 | A1 | 4/2007 | Liu et al. |
| 2015/0082872 | A1 | 3/2015 | Von Herzen et al. |
| 2016/0139104 | A1 | 5/2016 | Massey et al. |

FOREIGN PATENT DOCUMENTS

| | | |
|---|---|---|
| DE | 10245271 A1 | 4/2004 |
| DE | 102005032050 A1 | 1/2007 |
| DE | 102007037525 A1 | 2/2009 |
| JP | 3167242 U | 4/2011 |
| WO | 200231323 A1 | 4/2002 |
| WO | 2009039920 A1 | 4/2009 |

* cited by examiner

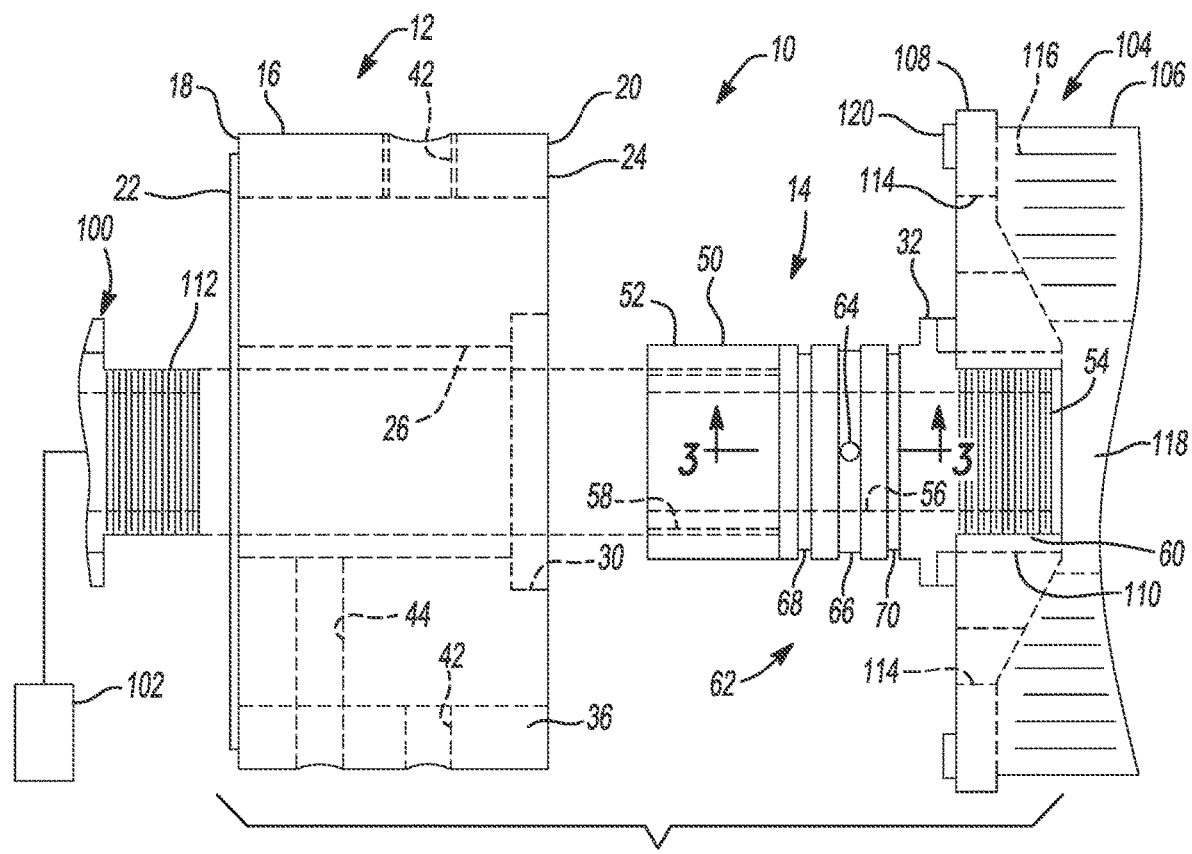
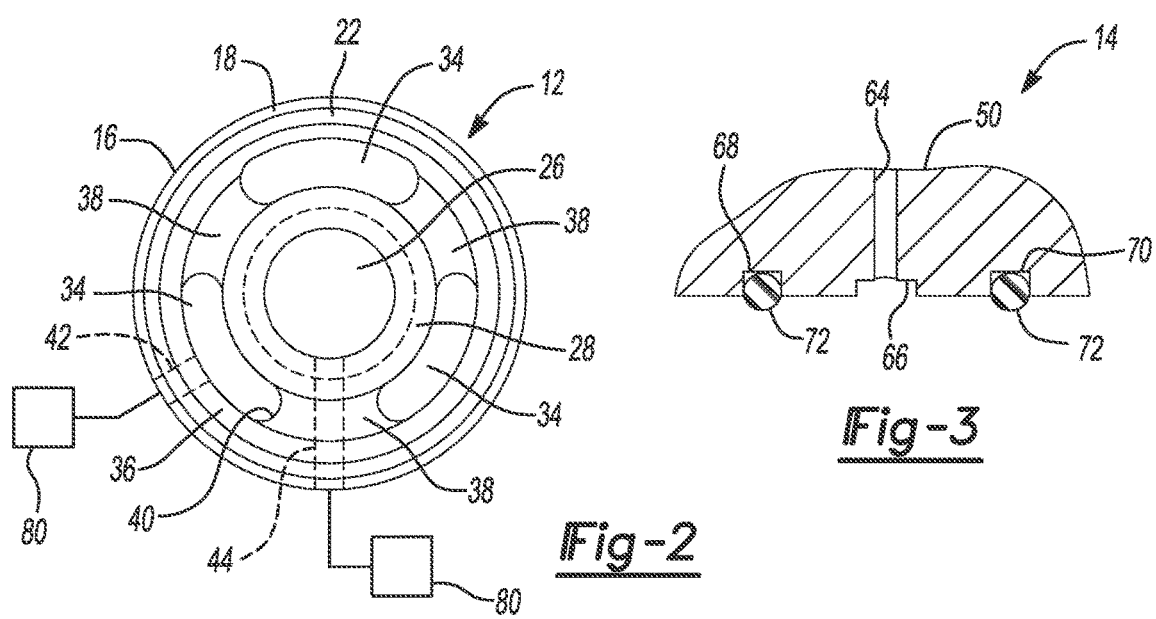

SYSTEMS FOR IN SITU MONITORING OF WORKING FLUIDS AND WORKING FLUID SYSTEMS

CROSS-REFERENCE TO RELATED APPLICATIONS

This application claims the benefit of U.S. Provisional Application No. 62/431,101, filed on Dec. 7, 2016, the entire contents of which are incorporated herein by reference.

FIELD

The present disclosure relates to systems for in situ monitoring of working fluids and working fluid systems and, more particularly, relates to an oil filters and adapters thereto configured to receive one or more sensors for monitoring an engine oil circulation system.

BACKGROUND

This section provides background information related to the present disclosure which is not necessarily prior art.

For many decades, engines have employed an oil-based lubrication system. Traditional lubrication systems provide fresh oil, within a predetermined temperature range and appropriate pressure, to each part of the engine. The oil is typically pumped from an oil sump through an oil filter, where it is strained or otherwise filtered for contaminants, and is often routed to the main bearings, along passages formed in the crankshaft and near connecting rods and along piston-cylinder regions. The piston-pin and cylinder walls received lubrication oil being dispersed by splash from the rotating crankshaft. Each camshaft bearing is fed by the main supply passage from a branch or tributary. During pumping, the oil cools and lubricates the engine and carries the contaminants to the oil filter and is cooled by the oil cooler or other cooling system, where the heat is transferred to the surrounding air.

As can be appreciated, monitoring of the engine oil and lubrication system is vital to reliable operation of the engine. In the event that lubrication oil pressure is lost, the engine can suffer from reduced and/or minimal oil flow that can prevent adequate cooling and lubrication of the engine. Similarly, in the event that a failure occurs in the lubrication system, such as due to a clogged oil filter, oil pump failure, or obstruction, it is important that detection of the failure is quick and reliable to permit mitigating actions to avoid permanent damage to the engine or sub component systems.

Although instrumentation is likely to provide a reliable and capable response system to such failures, it can be difficult to instrument an existing engine. To obtain access to the lubrication system for temperature, pressure, or other monitoring, one must be able to provide sensors in operational proximity to the lubrication system. In some cases, this requires a sensor to be placed in the oil stream or pathway. However, modern engines are not easily modified to accommodate such sensors. Moreover, redesigning engines to accommodate such sensors can results in substantial cost increases.

Accordingly, there exists a need in the relevant art to provide a system for permitting the monitoring of the lubrication system of the engine. Furthermore, there exists a need in the relevant art to provide a solution to permit modification of an existing engine to provide enhanced lubrication system monitoring. Still further, there exists a need in the relevant art to provide an adapter and/or canister solution to permit quick and convenient addition of sensor instruments to oil filters and/or canisters. Finally, there exists a need in the relevant art to provide a solution for providing sensor monitoring of the lubrication system of an engine that overcomes the disadvantages of the prior art.

SUMMARY

This section provides a general summary of the disclosure, and is not a comprehensive disclosure of its full scope or all of its features.

A working fluid monitoring system for monitoring a working fluid of working fluid system of a piece of equipment is provided. The working fluid monitoring system can include a filter member having an inlet, an outlet, and a filter media disposed between the inlet and the outlet. The filter member can be configured to permit fluid communication of the working fluid of the working fluid system from the inlet, through the filter media, and out the outlet of the filter member. A sensor is in operable communication with the working fluid within the filter member and is configured to monitor in situ a parameter of the working fluid and/or the working fluid system.

An oil filter adapter assembly for monitoring oil parameters of a lubrication system of an engine is provided. The engine can include an oil filter stud and an associated oil filter. The oil filter adapter assembly can comprise an adapter having a body with a proximal face and a distal face. The proximal face sealingly engages the engine and the distal face sealingly engages the oil filter. The adapter includes a central bore and an annular passageway, wherein the annular passageway fluidly couples the lubrication system of the engine and the oil filter and receives oil therein. A first pressure port fluidly extends from an exterior of the adapter to the annular passageway and is configured to be operably coupled to a sensor. The fastener includes a body defining a retaining feature. The proximal end of the fastener includes a threaded portion configured to threadedly engage the oil filter stud of the engine such that the retaining feature captures the adapter and retains the adapter in sealing engagement with the engine. The distal end of the fastener includes a threaded portion to threadedly engage the oil filter. The fastener further having a central oil passageway to fluidly couple the lubrication system of the engine and the oil filter and receive oil therein.

An oil filter adapter assembly for monitoring oil parameters of a lubrication system of an engine is also provided having an alternative configuration. The oil filter adapter assembly can comprise an adapter having a body with a proximal face and a distal face. The proximal face sealingly engages the engine and the distal face sealingly engages the oil filter. The adapter includes a central bore and an annular passageway, wherein the annular passageway fluidly couples the lubrication system of the engine and the oil filter and receives oil therein. The fastener includes a body defining a retaining feature. The proximal end of the fastener includes a threaded portion configured to threadedly engage the oil filter stud of the engine such that the retaining feature captures the adapter and retains the adapter in sealing engagement with the engine. The distal end of the fastener includes a threaded portion to threadedly engage the oil filter. The fastener further having a central oil passageway to fluidly couple the lubrication system of the engine and the oil filter and receive oil therein. A first pressure port fluidly extends from an exterior of the fastener to the central oil passageway. The first pressure port operably couples to a sensor via a communication port in fluid communication with the first pressure port.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only and not all possible implementations, and are not intended to limit the scope of the present disclosure.

FIG. 1 is an exploded view, with portion in cross-section, of an oil filter adapter assembly;

FIG. 2 is a proximal end view of the adapter;

FIG. 3 is a partial view cross-sectional of the pressure port extending through the fastener taken along lines 3-3 of FIG. 1;

Corresponding reference numerals indicate corresponding parts throughout the several views of the drawings.

DETAILED DESCRIPTION

Figure 4:
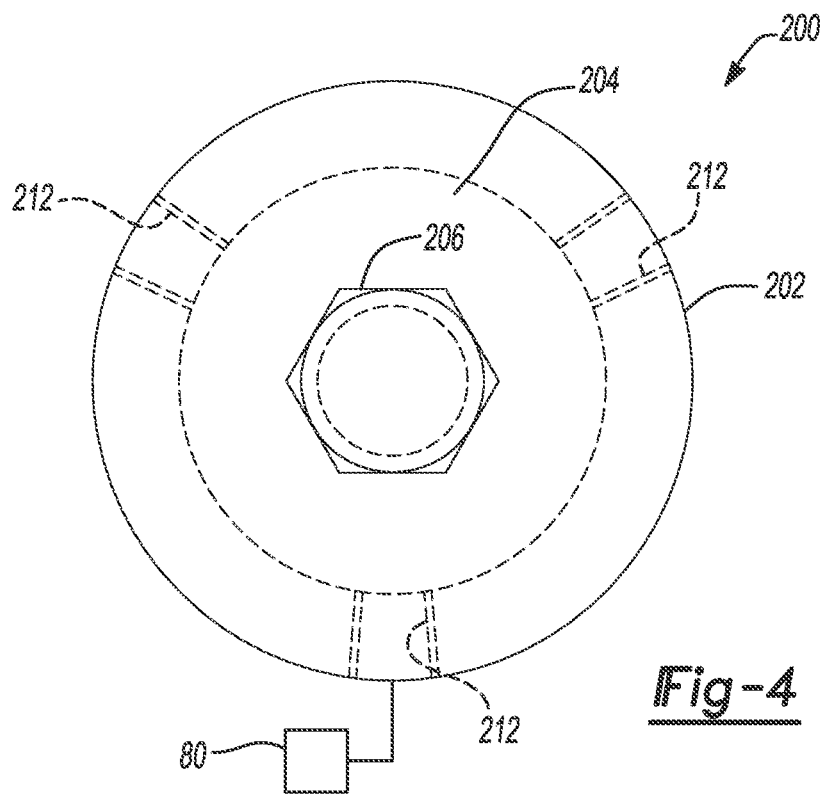
FIG. 4 is a top view of a canister cap assembly.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the present teachings, a working fluid monitoring system for monitoring a working fluid of working fluid system of a piece of equipment is provided. The working fluid monitoring system can include a filter member having an inlet, an outlet, and a filter media disposed between the inlet and the outlet. The filter member can be configured to permit fluid communication of the working fluid of the working fluid system from the inlet, through the filter media, and out the outlet of the filter member. A sensor is in operable communication with the working fluid within the filter member and is configured to monitor in situ a parameter of the working fluid and/or the working fluid system.

The working fluid monitoring system can include an oil filter adapter assembly for monitoring oil parameters of a lubrication system of an engine. The engine can include an oil filter stud and an associated oil filter. The oil filter adapter assembly can comprise an adapter having a body with a proximal face and a distal face. The proximal face sealingly engages the engine and the distal face sealingly engages the oil filter. The adapter includes a central bore and an annular passageway, wherein the annular passageway fluidly couples the lubrication system of the engine and the oil filter and receives oil therein. A first pressure port fluidly extends from an exterior of the adapter to the annular passageway and is configured to be operably coupled to a sensor. The fastener includes a body defining a retaining feature. The proximal end of the fastener includes a threaded portion configured to threadedly engage the oil filter stud of the engine such that the retaining feature captures the adapter and retains the adapter in sealing engagement with the engine. The distal end of the fastener includes a threaded portion to threadedly engage the oil filter. The fastener further having a central oil passageway to fluidly couple the lubrication system of the engine and the oil filter and receive oil therein With particular reference to the figures, FIG. 1 illustrates an oil filter adapter assembly 10 for use with engine 100 to permit addition and instrumentation of a lubrication or working fluid system system 102. Although the present teachings will be described in connection with engine 100 in the interest of brevity, it should be understood that the present application should not be regarded as being limited to only applications and uses requiring an engine. By way of non-limiting example, the present teaching may provide utility in a wide variety of applications, including marine, agricultural, industrial, or any application benefiting from fluid monitoring, such as, but not limited to, heavy machinery, semi-truck, jet engines, power plants, turbines, and the like. In the interest of brevity, the present disclosure will be made in connection with a conventional engine, but it should not be limited thereto.

Notwithstanding, lubrication system 102 of engine 100 can be a conventional lubrication system having one or more of a sump, oil pump, oil lines, oil spurt holes and galleries, pressure relief valve, and an oil filter 104. Lubrication system 102 is configured to pump, filter, cool, and distribute oil or other working fluid throughout engine 100.

Engine 100 can include oil filter 104, such as a spin-on oil filter, or other filter member for filtering a working fluid, such as oil. Filter 104 can be permanent or replaceable. In some embodiments, oil filter 104 is a conventional oil filter having a shell 106 coupled to a baseplate 108. Baseplate 108 can comprise a threaded portion 110 configured to threadedly engage a corresponding threaded oil filter stud 112 formed on and extending from engine 100. Oil filter 104 can further comprising one or more oil inlet ports 114 for receiving oil from engine 100 (also known as "used" oil as it may contain contaminants picked up within the lubrication system 102 of engine 100). Oil inlet ports 114 are in fluid communication with an interior volume of shell 106 of oil filter 104. The interior volume of shell 106 having a filter media 116 for filtering the used oil. Filter media 116 is disposed between inlet ports 114 and at least one outlet channel and port 118 for outputting oil to engine 100 (also known as "fresh" oil as it has been filtered by filter media 116).

With particular reference to FIGS. 1-3, oil filter adapter assembly 10 can comprise an adapter 12 and a threaded fastener 14. Threaded fastener 14 is configured to be threadedly coupled to oil filter stud 112 extending from engine 100 and retain adapter 12 in fluid sealing engagement with engine 100 or other structure thereof. As will be described herein, threaded fastener 14 is further configured to be threadedly coupled to threaded portion 110 of baseplate 108 of oil filter 104 such that oil filter 104 is in fluid sealing engagement with adapter 12. In this way, adapter 12 can be sealingly positioned between engine 100 and oil filter 104.

In some embodiments, as illustrated in FIGS. 1 and 2, adapter 12 is substantially cylindrical in cross-section having a body 16 having proximal end face 18 and distal end face 20. Body 16 can be sized and configured such that proximal end face 18 of body 16 is sized and shaped to sealing engage corresponding conventional structure on engine 100. To this end, adapter 12 can comprise an engine seal member 22 extending circumferentially around and captured by proximal end face 18 of body 16. Likewise, body 16 can be sized and configured such that distal end face 20 of body 16 is sized and shaped to sealing engage corresponding conventional structure on oil filter 104. To this end, adapter 12 can comprise a generally flat, smooth receiving land 24 for receiving a corresponding seal member 120 extending circumferentially around and captured by base plate 108 of oil filter 104.

With continued reference to FIGS. 1 and 2, in some embodiments, adapter 12 can further comprise at least one central port, channel, or bore 26 for receiving fastener 14 therein. To this end, central bore 26 can be cylindrical having an outer wall 28 (FIG. 2) circumferentially surrounding central bore 26. An inner diameter of central bore 26 can closely conform to an outer diameter of fastener 14, as will be described herein. Central bore 26 can further include a chamfer or shoulder depression 30 formed on distal end face 20 of body 16 for receiving a retaining feature or enlarged flange portion 32 of fastener 14. In some embodiments, a depth of depression 30 can be sized to permit flange portion 32 to be received therein such that flange portion 32 does not extend beyond distal end face 20.

In some embodiments, adapter 12 includes one or more annular passageways 34 for providing fluid communication of used oil from lubrication system 102 of engine 100 to oil inlet ports 114 of oil filter 104. Annular passageways 34 can be generally kidney shaped or any other shape and extend from proximal end face 18 to distal end face 20 to provide such fluid communication. In some embodiments, annular passageways 34 comprise three ports contained within an annulus area between outer wall 28 of central bore 26 and an outer wall 36 of body 16. In this way, radial spokes 38 are formed extending radially from outer wall 28 of central bore 26 to outer wall 36 of body 16. Annular passageways 34 can comprise generally curved or arcuate end walls 40 to minimize stress concentrations and/or fluid flow disruptions.

In some embodiments, one or more sensor ports can be disposed within adapter 12 to provide fluid communication with at least central bore 26 and/or one or more annular passageways 34. In some embodiments, a first or used oil pressure port 42 can extend from an exterior side of outer wall 36 of body 16 to an interior volume of at least one annular passageway 34. First pressure port 42 provides fluidic access to oil contained within annular passageway 34 flowing from engine 100 to oil filter 104. As will be described herein, access to this oil flow provides corresponding access to number of unique oil parameters not previously accessible in existing engine designs. It should be understood that additional ports can be provided extending from exterior side of outer wall 36 of body 16 to the interior volume of any annular passageway 34 for additional measurements and monitoring.

Similarly, in some embodiments, a second or fresh oil communication port 44 can extend from an exterior side of outer wall 36 of body 16, through at least one radial spoke 38, to an interior volume of central bore 26. As will be described herein, communication port 44 provides, at least in part, fluidic access to oil contained within a central oil passageway of oil filter 104 to engine 100. Communication port 44 can enable access to fresh oil measurements and monitoring immediately downstream of oil filter 104 (and particularly, filter media 116). It should be understood that additional ports can be provided extending from exterior side of outer wall 36 of body 16 to the interior volume of central bore 26 for additional measurements and monitoring.

First pressure port 42 and communication port 44 can comprise any one or a number of fastening interfaces, such as a threaded feature, mounting feature, coupling feature, or the like to permit operable coupling of one or more sensors thereto.

With particular reference to FIGS. 1 and 3, in some embodiments, fastener 14 is substantially cylindrical in cross-section having a body 50 having proximal end 52 and distal end 54. In some embodiments, body 50 comprises a central oil passageway 56 extending from proximal end 52 to distal end 54. In some embodiments, central oil passageway 56 is sized and configured to define an inner diameter and/or cross-sectional area sufficient to permit unobstructed passage of fresh oil from oil filter 104 to lubrication system 102 of engine 100. In some embodiments, a size of central oil passageway 56 closely resembles a corresponding passageway 122 formed in oil filter stud 112 of engine 100. Proximal end 52 of body 50 of fastener 14 can comprise a threaded female portion 58 being sized and shaped to threadedly engage oil filter stud 112 of engine 100. In this way, fastener 14 can threadingly engage oil filter stud 112 and capture adapter 12 in sealing engagement with engine 100 such that flange portion 32 of fastener 14 is received within depression 30 of adapter 12, thereby exerting a retaining force upon adapter 12 to maintain fluidic sealing engagement of adapter 12 with engine 100. In some embodiments, flange portion 32 includes features thereon to permit engagement by a work implement, such as a wrench or socket to facilitate engagement with engine 100.

Still further, fastener 14 can comprise an opposing male threaded portion 60 on distal end 54 of body 50. In some embodiments, male threaded portion 60 is sized and shaped to threadedly engage base plate 108 of oil filter 104. In some embodiments, male threaded portion 60 is conventionally sized to correspond to conventional oil filters. In some embodiments, male threaded portion 60 can extend from distal end 54 to flange portion 32.

In some embodiments, fastener 14 comprises a mid-section area 62 generally between the proximal end 52 and distal end 54. Mid-section area 62 can define an outer diameter that closely conforms to the inner diameter of central bore 26 of adapter 12 to promote fluidic sealing, proper positioning of adapter 12, and secure retention of adapter 12. In some embodiments, mid-section area 62 comprises a second pressure port 64 extending from an exterior surface of body 50 to central oil passageway 56 to permit fluid communication therethrough. In some embodiments, second pressure port 64 is configured to be in fluid communication with communication port 44 of adapter 12 to enable access to fresh oil measurements and monitoring immediately downstream of oil filter 104 (and particularly, filter media 116). To this end and to permit irrespective radial alignment of second pressure port 64 and communication port 44, fastener 14 can comprise a fluidic channel 66 circumferentially extending about the exterior surface of body 50 in a direction orthogonal to the longitudinal axis of body 50. In this way, once adapter 12 and fastener 14 are installed on engine 100, communication port 44 of adapter 12 is aligned with fluidic channel 66 of fastener 14 such that oil from second pressure port 64 can flow along fluidic channel 66 of fastener 14 and into communication port 44 of adapter 12. This oil can then be measured and monitored by a sensor via communication port 44. To ensure a fluid seal to prevent and/or minimize bypass of fluid, fastener 14 can comprise one or more sealing channels 68, 70 positioned on opposing sides of fluidic channel 66 and circumferentially extending about the exterior surface of body 50 in a direction orthogonal to the longitudinal axis of body 50. Sealing channels 68, 70 are sized and configured to receive a sealing member 72, such as an O-ring, of suitable thickness and durometer to sealing engage between body 50 of fastener 14 and central bore 26 of adapter 12.

It should be understood, however, that the present invention does not require port access to both the central oil passageway 56 and the annular passageways 34. In some embodiments, access to only one of the central oil passageway 56 and the annular passageways 34 may be desired. Therefore, it should be understood that in some embodiments it may be desirable to only provide first pressure port 42 or second pressure port 64 with communication port 44.

According to the principles of the present teachings, adapter 12 can be coupled with any one or a number of sensors 80. Sensor 80 can be disposed in operable communication with first pressure port 42 and/or communication port 44/second pressure port 64. Sensor 80 can be disposed within the flow of the working fluid or oil and/or disposed in fluid communication with working fluid or oil. It should be noted that sensor 80 can be coupled to provide direct communication with the working fluid or oil (e.g. within the flow of oil or within a port having direction communication with the working fluid or oil) or can be coupled to provide indirect communication with the working fluid or oil (e.g. separate from direct communication, but within operable range for measurement purposes). Sensor 80 can be used to measure, monitor, detect, or test the oil or other fluid in the lubrication system. This is particular advantageous for monitoring any one or a number of parameters of the oil, such as, but not limited to, the suspended soot, dielectric, conductivity, capacitance, total acid number, total base number, pH, oxidation, viscosity, flow rate, temperature, pressure, water, coolant, density, oil viscosity grade, VI, SSI (viscosity modifier shear stability), ferrous iron, fuel dilution, RGB color, florescence, phosphorescence, UV, infrared, X-ray, XRF, RF, refractive index, varnish, deposits, common wear metals (iron, lead, copper, aluminum, tin, vanadium, etc.), common components in a formulation (zinc, phosphorus, boron, calcium, magnesium, sulfur, etc.), particle count, air concentration, and the like. Sensor 80 can further be used to measure or monitor associated and/or nearby systems (e.g. working fluid system) that may result in a change in oil or fluid parameters, such as a coolant leak, faulty or failing oil pump, or the like.

It should be appreciated that the present design permits sufficient volume flow of oil through the combination of second pressure port 64, fluidic channel 66, and communication port 44 and also through first pressure port 42 to enable sensors 80 requiring increased volume flowrates to be used.

In some embodiments, as illustrated in FIGS. 4-8, the principles of the present teachings can further be employed in engines employing a canister filter assembly. As is known in the art, canister filter assemblies generally employ a canister housing 150 (FIG. 5) that is configured to remain installed in an engine compartment of a vehicle. According to canister filter designs, the canister housing and canister cap are intended to be reused and the filter media within the canister housing is then replaced on recommended intervals. However, as can be appreciated, there is a desire to measure and monitor oil properties as described herein. Unfortunately, the adapter 12 and fastener 14 configuration may not be applicable in connection with canister filter assemblies.

Accordingly, in some embodiments, a canister cap assembly 200 is provided for achieving the benefits of the present teachings in canister filter assemblies. In some embodiments, canister cap assembly 200 comprises a cap body 202 having a central dome feature 204 defining a drive nut 206 to facilitate threaded engagement of canister cap assembly 200 with canister housing 150. Canister cap assembly 200 comprises male threads 208 threadedly engaging corresponding female threads formed in canister housing 150. Canister cap assembly 200 is configured to threadedly engage canister housing 150 and form a fluid seal therebetween. To this end, canister cap assembly 200 can comprise a seal member 210 extending about a portion of cap body 202 in a location generally adjacent to male threads 208. Seal member 210 can comprise an O-ring of suitable thickness and durometer to provide sealing engagement between an outer surface of cap body 202 and an inner surface of canister housing 150.

Figure 5:
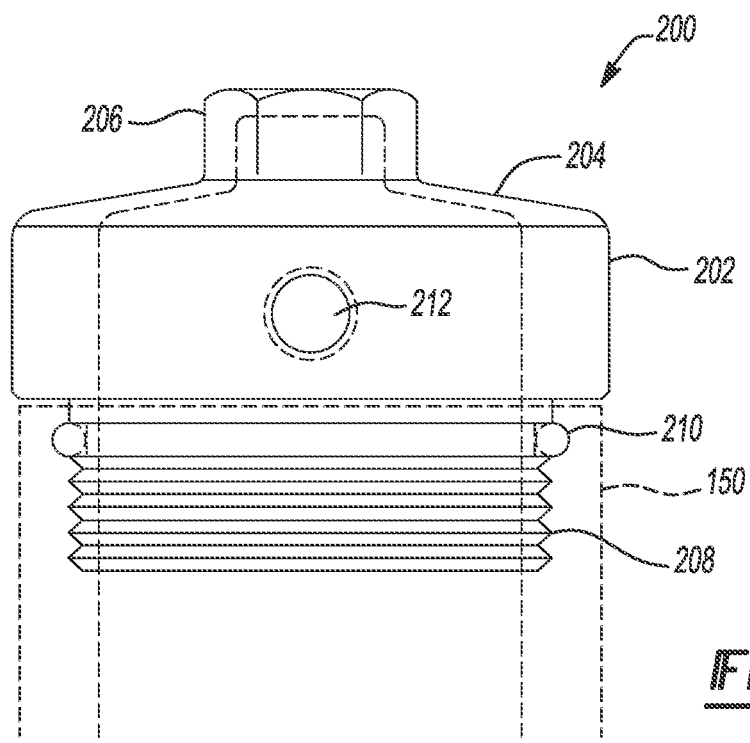
FIG. 5 is a side view of the canister cap assembly.

In some embodiments, as illustrated in FIGS. 4 and 5, canister cap assembly 200 can comprise one or more pressure ports 212 extending through cap body 202 from an exterior surface to an interior volume of canister housing 150. Pressure port 212 provides fluidic access to oil contained within canister housing 150 flowing to/from engine 100. Access to this oil flow provides corresponding access to number of unique oil parameters not previously accessible in existing canister filter designs. It should be understood that additional ports can be provided extending from exterior side of cap body 202 to the interior volume of canister housing 150 for additional measurements and monitoring.

Figure 6:
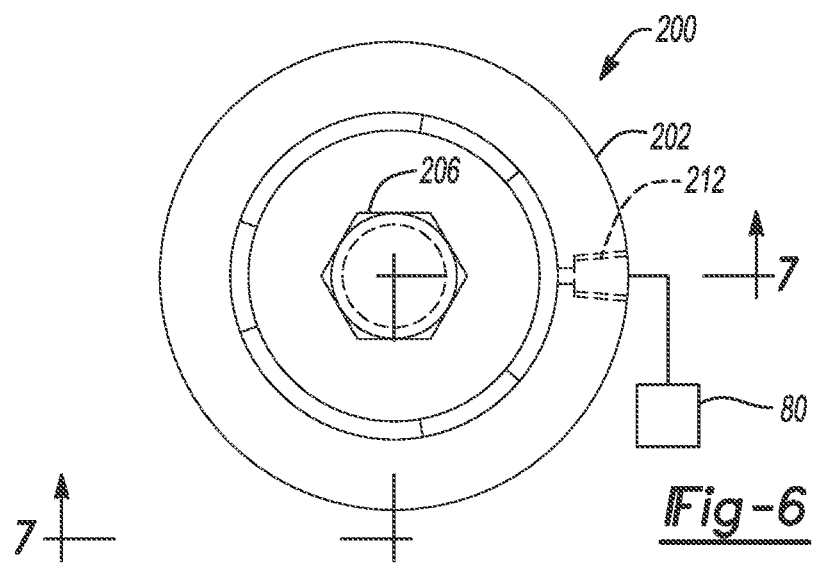
FIG. 6 is a top view of a canister cap assembly.
Figure 7:
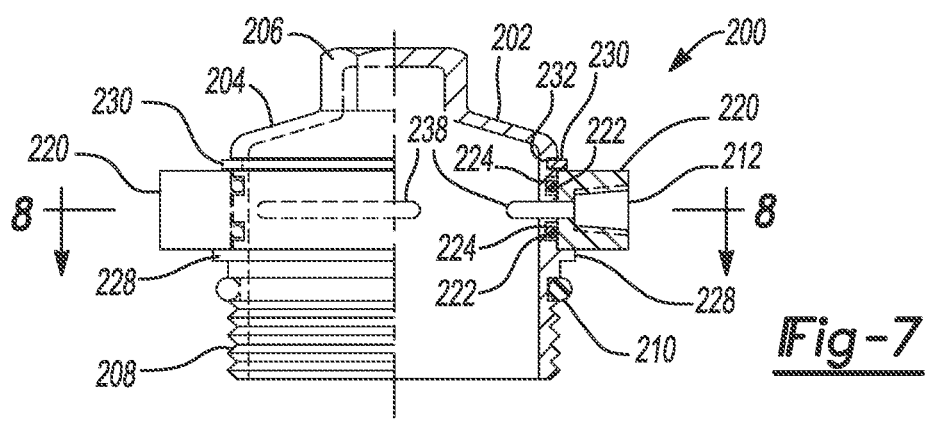
FIG. 7 is a cross-sectional view of the canister cap assembly of FIG. 6 taken along lines 7-7 of FIG. 6.
Figure 8:
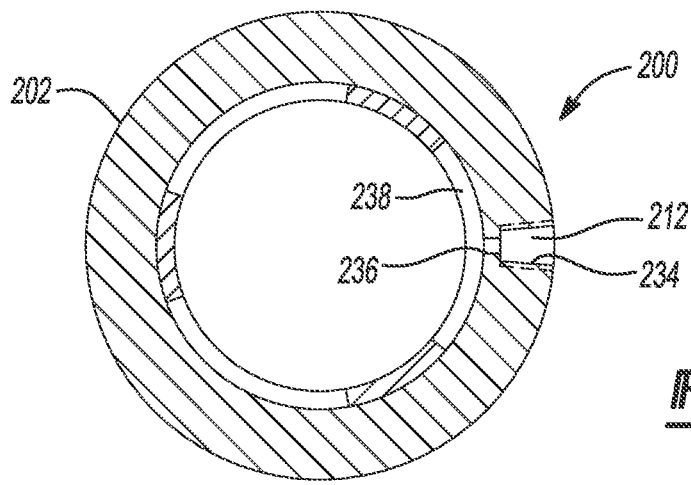
FIG. 8 is a cross-sectional view of the canister cap assembly of FIG. 6 taken along lines 8-8 of FIG. 7.

In some embodiments, as illustrated in FIGS. 6-8, canister cap assembly 200 can comprise an adjustable sleeve 220 extending circumferentially about cap body 202. Sleeve 220 can engage cap body 202 to form a fluid seal therebetween. In some embodiments, sleeve 220 can comprise one or more seal members 222, such as O-rings, disposed between cap body 202 and sleeve 220 and received with sealing channels 224, 226. Sleeve 220 can be a continuous circular member retained on cap body 202 by a flange ledge 228 extending from cap body 202 and a releasable snap ring member 230 received within a snap-ring groove 232 formed in cap body 202.

In some embodiments, sleeve 220 can comprise a pressure port 212 in fluid communication with the interior volume of canister housing 150. In some embodiments, pressure port 212 comprises a first portion 234 being generally conical and in fluid communication with a second portion 236 extending between first portion 234 and third portion 238. Second portion 236 can be a generally cylindrical port and third portion 238 can be an elongated slot extending circumferentially about at least a portion of the inner surface of cap body 202. In this way, third portion 238 can be in fluid communication with a larger portion of the interior volume of canister housing 150.

As should be appreciated from the foregoing, the principles of the present teachings provide the unique capability of quickly and conveniently configuring a lubrication system of an engine to include one or more sensors for measurement, detection, monitoring, and testing of oil within the lubrication system. Obtaining this data can permit continuous, rapid, and real-time notification of system malfunctions and failures. Moreover, these benefits can be obtained in existing engines without substantial modification and/or redesign.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. An oil filter adapter assembly for monitoring oil parameters of a lubrication system of an engine, the engine having an oil filter stud and an associated oil filter, the oil filter adapter assembly comprising: an adapter having a body having a proximal face and a distal face, the proximal face sealingly engageable with the engine and the distal face sealingly engageable with the associated oil filter, the adapter further having a central bore and an annular passageway, the annular passageway being configured to fluidly couple the lubrication system of the engine and the associated oil filter and receive oil therein; and a fastener having a body defining a retaining feature, the fastener having a proximal end and a distal end, the proximal end having a threaded portion configured to threadedly engage the oil filter stud of the engine such that the retaining feature captures the adapter and retains the adapter in sealing engagement with the engine, the distal end having a threaded portion configured to threadedly engage the associated oil filter, the fastener further having a central oil passageway being configured to fluidly couple the lubrication system of the engine and the associated oil filter and receive oil therein, a first pressure port fluidly extending from an exterior of the fastener to the central oil passageway, the first pressure port configured to be operably coupled to a sensor via a communication port in fluid communication with the first pressure port.

2. The oil filter adapter assembly according to claim 1, wherein the communication port extends from the exterior of the adapter to the first pressure port.

3. The oil filter adapter assembly according to claim 1, further comprising a sealing member extending from the proximal face of the body of the adapter configured to be engaged with the engine.

* * * * *